United States Patent [19]

Ishibe

[11] 4,424,386

[45] Jan. 3, 1984

[54] METHYLCHLOROFORM STABILIZER COMPOSITIONS EMPLOYING THIAZOLIDINE

[75] Inventor: Nobuyuki Ishibe, Lake Jackson, Tex.

[73] Assignee: The Dow Chemical Company, Midland, Mich.

[21] Appl. No.: 300,715

[22] Filed: Sep. 10, 1981

[51] Int. Cl.³ .............................................. C07C 17/42
[52] U.S. Cl. .................................... 570/109; 570/111; 570/120; 252/391
[58] Field of Search ....................... 570/120, 109, 111; 252/391, 402

[56] References Cited

U.S. PATENT DOCUMENTS

| | | | |
|---|---|---|---|
| 2,316,011 | 4/1943 | Miller et al. ........................ | 252/402 |
| 3,535,392 | 10/1970 | Cormany ............................. | 570/120 |
| 3,609,091 | 9/1971 | Harden et al. ...................... | 570/111 |
| 3,641,169 | 2/1972 | Crabb et al. ........................ | 570/120 |
| 3,763,048 | 10/1973 | Nishihara et al. ................... | 570/120 |
| 3,798,170 | 3/1974 | Petering et al. ..................... | 570/109 |
| 4,069,265 | 1/1978 | Richtzenhain et al. .............. | 570/111 |
| 4,189,397 | 2/1980 | Allen .................................. | 570/109 |
| 4,309,301 | 1/1982 | Ishibe et al. ........................ | 570/120 |

*Primary Examiner*—Anton H. Sutto
*Assistant Examiner*—Joseph A. Boska
*Attorney, Agent, or Firm*—A. Cooper Ancona

[57] ABSTRACT

Metal corrosion in the presence of methylchloroform is inhibited when thiazolidine is added to the methylchloroform. The inhibitor is useful in degreasing processes and may be used in combination with other known inhibitors.

4 Claims, No Drawings

METHYLCHLOROFORM STABILIZER COMPOSITIONS EMPLOYING THIAZOLIDINE

BACKGROUND OF THE INVENTION

Numerous compounds, including ethers, cyclic ethers, alcohols, including aliphatic, olefinic and acetylenic varieties, nitroalkanes, esters, and others have been employed in various combinations to stabilize the chlorinated hydrocarbons in the presence of various metals.

Sulfur-containing compounds have also been employed as stabilizers for methylchloroform, e.g. mercaptans and disulfides have been used as secondary inhibitors (U.S. Pat. No. 3,641,169) to prevent the reaction of acids with the epoxides employed as stabilizers. Such acids are frequently found in metal cleaning operations. Sulfoxides have also been taught as useful in combination with epoxides (U.S. Pat. No. 3,535,392) as stabilizers for methylchloroform. Dithianes and thioxanes are taught to stabilize methylchloroform against reaction with iron and aluminum (U.S. Pat. No. 3,384,673). Other sulfur compounds are disclosed as useful stabilizers in U.S. Pat. Nos. 3,439,051 (dithiin); 3,467,722 (trimethylene sulfide); and 3,763,048 (1,3-dithiolane, 1,3-oxathiolane).

Nitrogen-containing compounds useful in the stabilization of methylchloroform which have been taught as useful in various combinations are the nitroalkanes, as previously mentioned; nitriles, such as acetonitrile (U.S. Pat. No. 3,445,532) or alkyl cyanides (U.S. Pat. No. 3,564,061); cyclic nitrogen compounds, such as pyrrole, aziridine and their alkyl derivatives. U.S. Pat. No. 3,551,505 employs the combination of an alkyl pyrrole and a diaziridine as a stabilizer for methylchloroform. Cyano compounds, such as tetracyanoethylene and tetracyanodithiin are disclosed as stabilizers for chlorinated solvents, including methylchloroform, in U.S. Pat. No. 3,277,193.

It has now been found that a cyclic compound, thiazolidine, which contains both nitrogen and sulfur is an effective stabilizer for methylchloroform. Thiazolidine (TZN) has the formula $C_3H_7NS$ and the structure

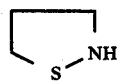

It can be used alone or in combination with other known stabilizers. The stabilizer is effective against aluminum, zinc, iron, copper, steel and brass and is especially effective under the conditions encountered in vapor degreasing operations.

SUMMARY OF THE INVENTION

Thiazolidine is useful as an inhibitor against metal corrosion when used in methylchloroform which is in contact with metals. It is useful alone or its inhibitory power can be enhanced by its combination with other known inhibitors, especially nitroalkanes, alkyl nitrates, alkyl cyanides, acetylenic alcohols and aliphatic epoxides. It is especially useful when methylchloroform is employed in degreasing processes.

DETAILED DESCRIPTION OF THE INVENTION

Thiazolidine has been found to be a very effective stabilizer for methylchloroform singly or in combination with other additives. All metals studied were effectively protected from corrosion. Use of thiazolidine alone can eliminate the need for dioxane, epoxides, and nitroalkanes which are used commercially as stabilizers in methylchloroform. It can also be employed with any one or more of these without deleterious effect.

Thiazolidine can be employed alone to stabilize methylchloroform and when so used should be present in a concentration of from about 0.5 to about 5 volume percent in the stabilized solvent. The preferred concentration is from about 2 to about 4 volume percent.

When used in combination with another inhibitor, e.g. a nitroalkane, the thiazolidine is employed at a concentration of from 0.5 to 5 percent and the other inhibitor at from 1 to 5 percent by volume based on the total volume of the stabilizers and solvent.

The nitroalkanes and alkyl nitrates useful are those containing from one to three carbon atoms. Thus, methyl, ethyl, propyl and isopropyl nitrates are effective and nitromethane, nitroethane and nitropropanes may be employed.

Alkyl cyanides such as methylcyanide (acetonitrile), acrylonitrile, propionitrile and the like may be used in combination with thiazolidine. The acetylenic alcohols useful are those having from 3 to 5 carbon atoms, e.g. 2-propyn-1-ol, 3-butyn-1-ol, 2-butyn-1-ol, 1-methyl-3-butyn-1-ol, 2-methyl-3-butyn-1-ol, 1-methyl-2-propyn-1-ol, and the like. Epoxides useful in the combination are propylene and butylene oxides.

Pyrazine can also be used in combination with thiazolidine in vapor degreasing operations and is especially useful in protecting aluminum in the dip section of a degreaser. The following examples illustrate the invention.

EXAMPLE 1

Approximately 430 g of methylchloroform solution formulated with thiazolidine singly or in combination with other additives was partitioned by distillation into equal volume fractions. Ten ml aliquots of both fractionated (top and bottom) and unfractionated solutions were refluxed for seven days in the presence of Al, Zn, Cu, brass, steel, and Fe metal coupons, chips or pellets, and the stability of the solution was rated. The number of hours to the start of corrosion or the end of the test is indicated. Results are given in Table I. Unfractionated (U) and fractionated bottom (B) solutions of thiazolidine itself protects all metals, whereas the fractionated top (T) solution fails with aluminum because of the high boiling point (73° C./25 mm Hg) of the thiazolidine. Addition of pyrazine (b.p. 115° C.), however, prevents corrosion of aluminum in the fractionated top solution (Run 2). Thiazolidine is compatible with various additives (Runs 3-7).

TABLE I

| Run No. | Vol. %* TZN | Vol. %* Other | Fraction | Metals | Time (hrs) |
|---|---|---|---|---|---|
| 1 | 3-4 | — | U | Al, Zn, Cu, Fe, Brass, Steel | >168 |
|  |  |  | B | Al, Zn, Cu, Fe, | >168 |

TABLE I-continued

| Run No. | Vol. %* TZN | Vol. %* Other | Fraction | Metals | Time (hrs) |
|---|---|---|---|---|---|
| | | | | Brass, Steel | |
| | | | T | Zn, Brass, Cu, Fe | >168 |
| | | | | Al | 24 |
| 2 | 0.5-2 | PZ | U | Al, Zn, Cu, Fe, Brass, Steel | >168 |
| | | | B | Al, Zn, Cu, Fe, Brass, Steel | >168 |
| | | | T | Al, Zn, Cu, Fe, Brass, Steel | 144 |
| 3 | 4 | NM 0.5 | U | Al, Zn | >168 |
| 4 | 4 | IPN 0.5 | U | Al, Zn | >168 |
| 5 | 4 | ACN 0.5 | U | Al, Zn | >168 |
| 6 | 4 | B.O. 0.5 | U | Al, Zn | >168 |
| 7 | 4 | BYL | U | Al, Zn | >168 |

*Vol. % is that amount in original stabilized solvent prior to fractionation.
PZ = pyrazine,
NM = nitromethane,
IPN = isopropyl nitrate,
ACN = acetonitrile,
B.O. = butylene oxide,
BYL = 3-butyn-1-ol.

I claim:

1. A stabilized methylchloroform composition consisting essentially of methylchloroform, a stabilizing amount of thiazolidine and, optionally, a stabilizing amount of a nitroalkane.

2. The composition of claim 1 wherein the nitroalkane contains from one to three carbon atoms.

3. The composition of claim 2 wherein the thiazolidine is present in an amount of from about 0.5 to about 5 percent and the nitroalkane is present in an amount of from about 1 to about 5 percent based on the total volume of the composition.

4. The composition of claim 3 wherein the nitroalkane is nitromethane.

* * * * *